United States Patent
Kunst

(10) Patent No.: US 7,955,441 B2
(45) Date of Patent: Jun. 7, 2011

(54) DEVICE AND METHOD FOR CLEANING MOULD PADDLES

(75) Inventor: Gerrit Hendrik Kunst, Rijssen (NL)

(73) Assignee: V.O.F. Demato, DW Rijssen (NL)

( * ) Notice: Subject to any disclaimer, the term of this patent is extended or adjusted under 35 U.S.C. 154(b) by 1137 days.

(21) Appl. No.: 10/483,372

(22) PCT Filed: Jul. 8, 2002

(86) PCT No.: PCT/NL02/00446
§ 371 (c)(1),
(2), (4) Date: Jun. 25, 2004

(87) PCT Pub. No.: WO03/006182
PCT Pub. Date: Jan. 23, 2003

(65) Prior Publication Data
US 2004/0231704 A1 Nov. 25, 2004

(30) Foreign Application Priority Data

Jul. 10, 2001 (NL) .................................... 1018503

(51) Int. Cl.
*B08B 3/06* (2006.01)
(52) U.S. Cl. ........................................... 134/33; 134/32
(58) Field of Classification Search .................. 134/10, 134/32, 33, 111, 176, 179, 166 R, 169 R, 134/31
See application file for complete search history.

(56) References Cited

U.S. PATENT DOCUMENTS

| | | | | |
|---|---|---|---|---|
| 3,853,622 A | * | 12/1974 | Rutten | 134/25.4 |
| 4,209,344 A | * | 6/1980 | Simon et al. | 134/23 |
| 4,300,581 A | * | 11/1981 | Thompson | 134/57 R |
| 5,173,122 A | * | 12/1992 | Tilby et al. | 127/2 |
| 5,758,675 A | * | 6/1998 | Scheyer | 134/148 |
| 6,390,104 B1 | * | 5/2002 | Gagnon | 134/107 |
| 6,558,620 B1 | * | 5/2003 | Sanford et al. | 422/28 |

FOREIGN PATENT DOCUMENTS

| | | |
|---|---|---|
| DE | 3608776 | * 10/1987 |
| DE | 3608776 A1 | 10/1987 |
| DE | 196 19 000 A1 | 11/1997 |
| EP | 0 614 618 A1 | 9/1994 |
| FR | 1 481 218 A1 | 8/1967 |
| FR | 1 570 302 A1 | 6/1969 |
| GB | 285556 | 2/1928 |
| WO | WO 98/17408 A1 | 4/1998 |

* cited by examiner

*Primary Examiner* — Michael Barr
*Assistant Examiner* — Saeed T Chaudhry
(74) *Attorney, Agent, or Firm* — The Webb Law Firm

(57) ABSTRACT

A device is disclosed for cleaning dental trays at least partly filled with a molding material. The device has a container, a pump for placing a cleaning liquid under pressure, and a spray nozzle for spraying the pressurized cleaning liquid into the container. A method is also disclosed for cleaning dental trays at least partly filled with a molding material.

1 Claim, 4 Drawing Sheets

DEVICE AND METHOD FOR CLEANING MOULD PADDLES

BACKGROUND OF THE INVENTION

1. Field of the Invention

The invention relates to a device for cleaning dental trays at least partly filled with a moulding material. Dental trays are used for instance by a dentist to make a mould of part of the teeth of a patient in order to have a crown, a bridge or a prosthesis made therewith by a dental technician. The dental tray is filled by the dentist shortly before use with a mixture of plaster, an elastic binder and water, which mixture sets in the mouth of the patient and therein forms the desired mould.

2. Description of the Related Art

Arriving daily at the premises of a dental technician are a large number of dental trays which, after being used, have to be cleaned. The superior material properties of the set mixture here represents a great drawback. The plaster has crystallized into hard particles which are embedded in the elastic binder. The whole structure is stuck fast to the dental tray. This is made even worse in that the dental tray is often provided with roughness or holes to increase adhesion, this to prevent the set mixture remaining adhered to the teeth of the patient instead of to the dental tray. The dental trays must nevertheless be cleaned, something which takes place by hand because there is no other alternative. To allow manual cleaning to proceed effectively use is made of cleaning agents which subsequently end up via the sewer in the environment. Even if cleaning agents are used, this remains time-consuming and unpleasant work.

SUMMARY OF THE INVENTION

The present invention obviates this drawback. It is based on the discovery that the set mixture does not stand up well to a jet of liquid sprayed thereon at very high pressure. The hard particles are herein broken loose from the matrix of elastic binder and the elastic binder also falls apart into small particles. The invention therefore has the feature that the device comprises a container in which dental trays for cleaning can be accommodated, a high-pressure pump for supplying a cleaning liquid under a high pressure, a spray head for spraying the cleaning liquid at least substantially in the direction of the dental trays, and filter means for separating cleaning liquid and mould material. Using the inventive device treated dental trays are completely clean within a few minutes, and they are damaged less during the cleaning so that they last longer. The material filtered out by the filter means can be periodically removed and disposed of.

A favourable embodiment of the inventive device has the feature that the cleaning liquid is water. The advantage is that the cleaning liquid can then be drained simply after use to the sewer without the environment being contaminated.

A further favourable embodiment of the inventive device has the feature that the container comprises a rotatably disposed drum. Due to the rotation the dental trays are in continuous movement, whereby every part of their surface is regularly struck by the water jet. The drum is preferably provided herein with openings and placed in a shell, so that used cleaning liquid and particles can readily leave the drum and be collected by the shell. The shell is then preferably provided with an outlet connected to the filter means.

A further preferred embodiment of the device has the feature that the drum is at least almost cylindrical in form, and that in the situation of use a longitudinal axis of the drum encloses an angle of thirty to sixty degrees with a horizontal plane. A thus placed drum gives good cleaning results and is moreover ergonomic and visually attractive.

In a further preferred embodiment an inner side of the drum is provided with a layer manufactured from an elastic material, for instance rubber. The noise caused by dental trays striking against each other and the drum can hereby be significantly damped.

In a further preferred embodiment the spray head is provided with a nozzle known as such in the field which rotates in the situation of use. In the present application it is precisely this combination of a rotating drum and a rotating nozzle which is found to result in a very short cleaning time.

The invention also relates to a method for cleaning dental trays at least partly filled with a moulding material. The inventive method has the feature that the dental trays are placed in an at least practically cylindrical container, that the container is rotated about a longitudinal axis, that the longitudinal axis encloses an angle of thirty to sixty degrees with a horizontal plane and that the dental trays are herein sprayed with a cleaning liquid under high pressure.

A favourable realization of the inventive method has the feature that the cleaning liquid is sprayed using a rotating nozzle.

BREIF DESCRIPTION OF THE DRAWINGS

The invention will now be further elucidated with reference to the following figures, wherein.

DETAILED DESCRIPTION OF THE INVENTION

Figure 1:
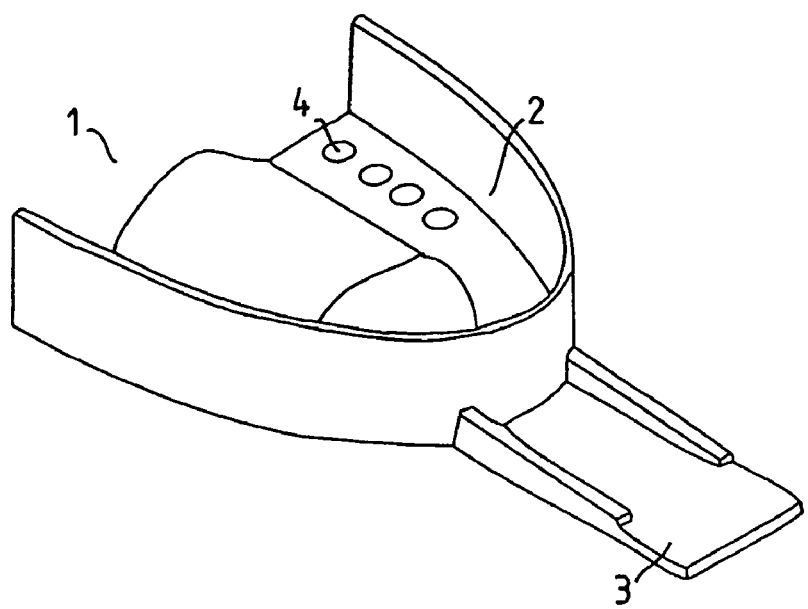
FIG. 1 shows in perspective a possible embodiment of a dental tray.

FIG. 1 shows in perspective a possible embodiment of a dental tray 1, consisting of a tray 2 manufactured from metal or a plastic in which the dentist's assistant arranges a mix of plaster, an elastic binder and water, whereafter the dentist arranges tray 2 round the upper teeth of a patient and holds the tray fixedly by a handle 3 until the mixture is sufficiently set. The thus obtained mould of the upper teeth is then jiggled loose, wherein the roughness or holes 4 in tray 2 ensure that the mould remains in position in tray 2.

The dental tray shown here is specifically for the upper teeth; for the lower teeth a slightly different dental tray is available which is employed in wholly similar manner. In addition, different sizes and different embodiments of dental trays 1 are available. In the cleaning of used dental trays, wherein the set mixture must be removed, it is not therefore possible to assume a pre-known form of the dental tray.

Figure 2:
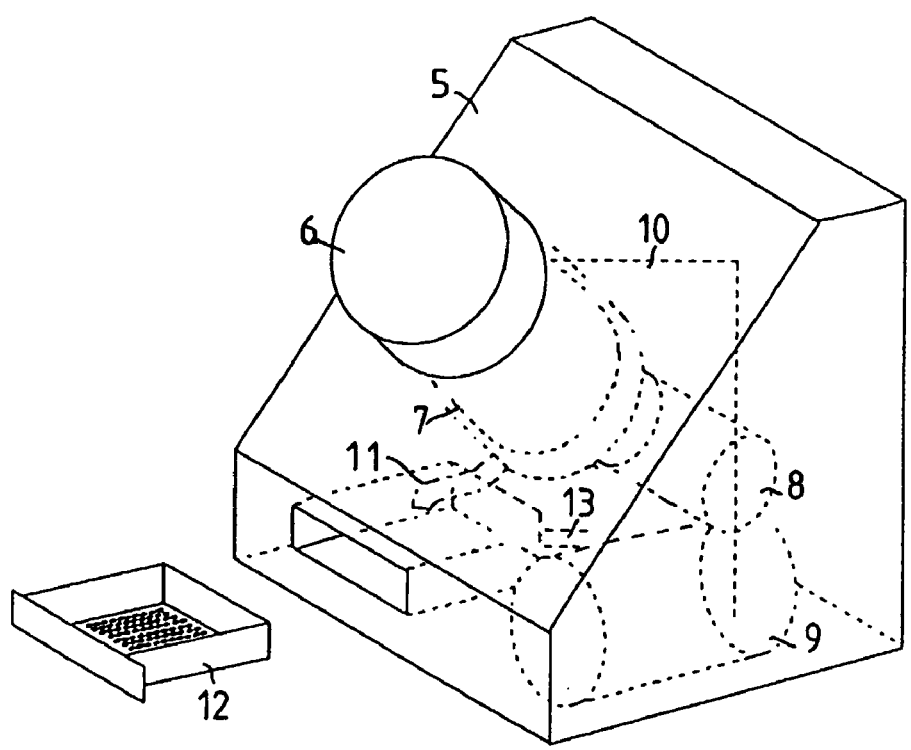
FIG. 2 shows schematically in perspective a possible embodiment of the inventive device.

FIG. 2 shows schematically in perspective a possible embodiment of the inventive device consisting of a housing 5 in which a shell 6 is placed at an angle of forty-five degrees, in which shell a round drum 7 is in turn placed. The dental trays for cleaning can be placed in drum 7, whereafter the upper side of shell 6 is closed with a cover or sealing cap (not shown). A motor 8 is then switched on which causes drum 7 to rotate slowly on its main axis, whereby the dental trays will tumble over each other. A high-pressure pump 9 is then switched on which, via a conduit 10 and a nozzle not shown in this figure, sprays a fine jet of water at the dental trays with great force. The set mixture herein disintegrates almost completely and is discharged together with the water via discharge openings in drum 7, shell 6 and via a pipe 11. Large chunks of set mixture can remain in drum 7, but most of the set mixture will end up in a sieve 12 which is shown here outside housing 5 for purposes of illustration. The water passes through sieve 12 and is drained via a drain pipe 13 to the sewer, optionally after having passed through a known second filter placed outside housing 5. The content of sieve 5 can be removed as normal waste. Recycling of the water or the set material is possible but not particularly desirable per se because it is contaminated with bacteria.

Figure 3:
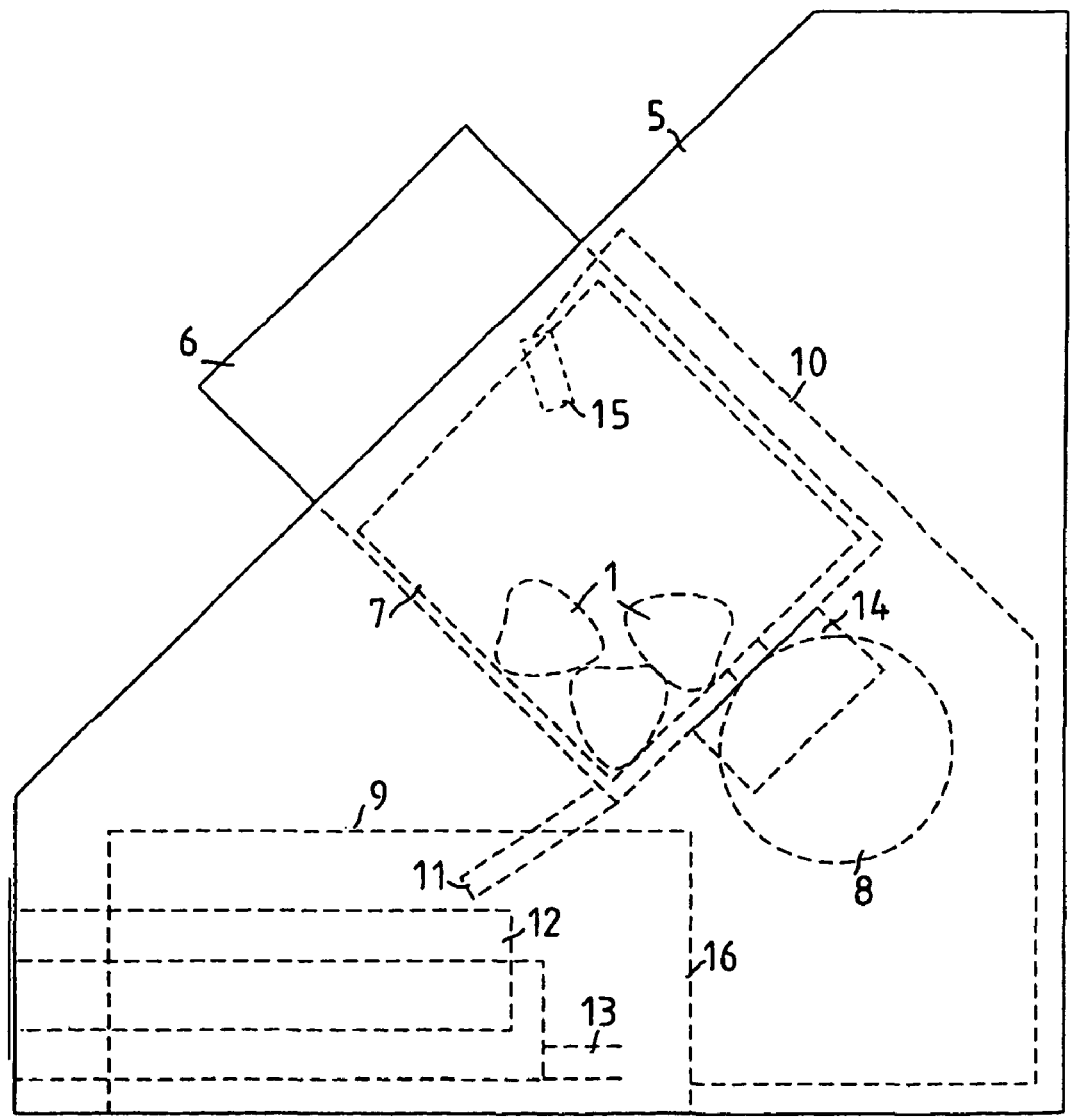
FIG. 3 shows this embodiment in schematic side view.

FIG. 3 shows this embodiment in schematic side view, with housing 5 in which shell 6 is placed, in which in turn a round drum 7 is placed. Motor 8 is coupled to drum 7 via a per se known reduction gear 14 which also comprises a right-angled transmission, provides the bearing of drum 7 and provides a moisture-tight sealing with shell 6. The reduction is chosen such that during use the drum 7 revolves roughly once every six seconds. Further shown is the electrically driven, per se known high-pressure pump 9 which can supply water at a pressure of about 100 bar, conduit 10 and a nozzle 15 which is aimed generally at the trays 1 for cleaning. In this figure sieve 12 has been pushed into housing 5 and is enclosed by a box 16 onto which is connected drain pipe 13 for draining filtered water.

Figure 4:
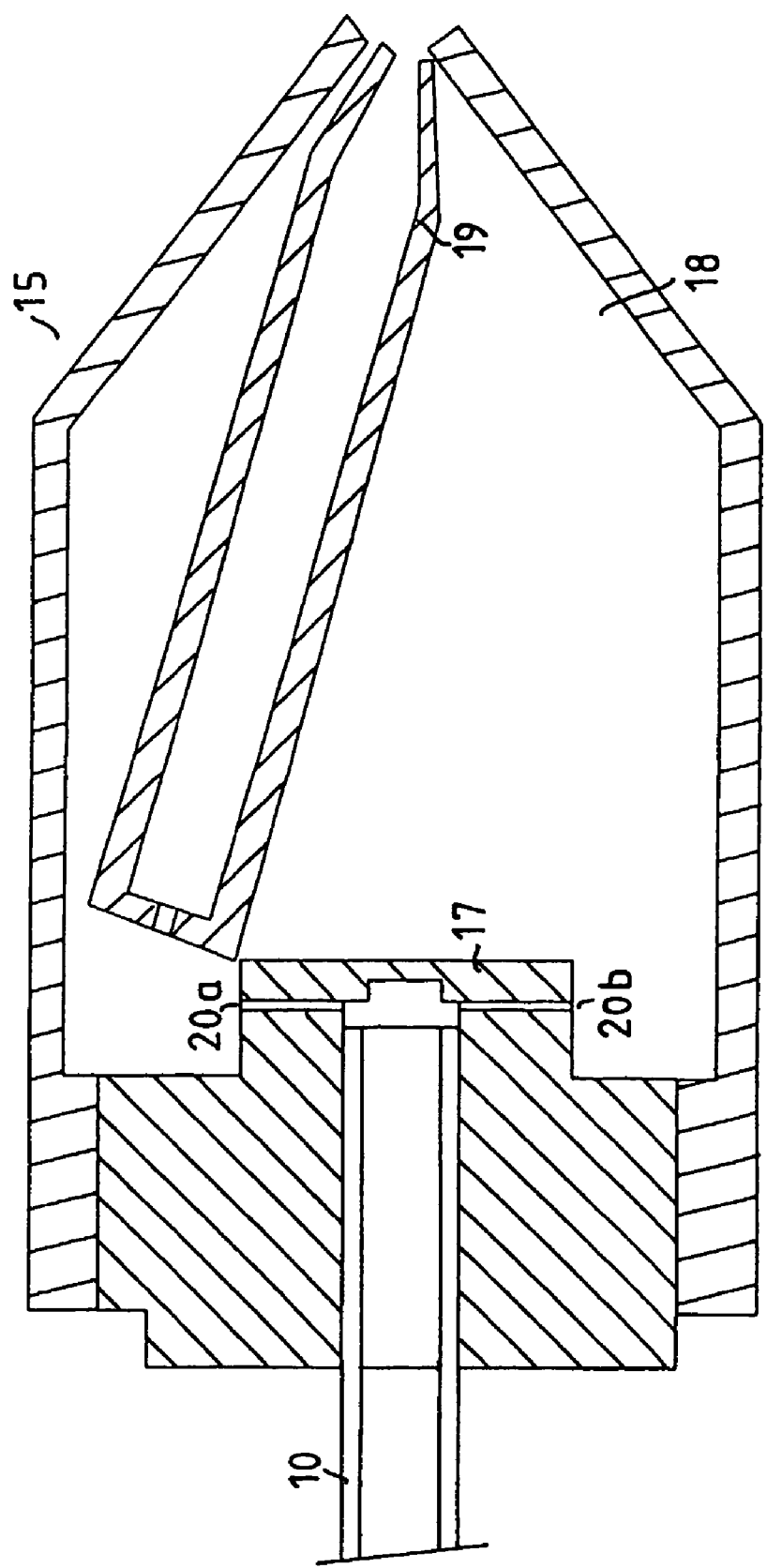
FIG. 4 shows a rotating nozzle in schematic side view.

FIG. 4 shows in schematic side view a possible embodiment of a per se known rotating nozzle 15. Via conduit 10 and a transition part 10 water is fed to a chamber 18 in which the actual nozzle 19 can rotate freely around transition part 17. Into transition part 17 are bored two holes 20a,20b which run slightly obliquely and therefore not radially, whereby a swirl is created in chamber 18 and nozzle 19 will begin to rotate. During use the jet of water generated by nozzle 19 will thereby pass through a conical plane. The combination of the rotating nozzle and a rotating drum 7 ensures that a water jet will periodically contact at every position a dental tray for cleaning.

Figure 5:
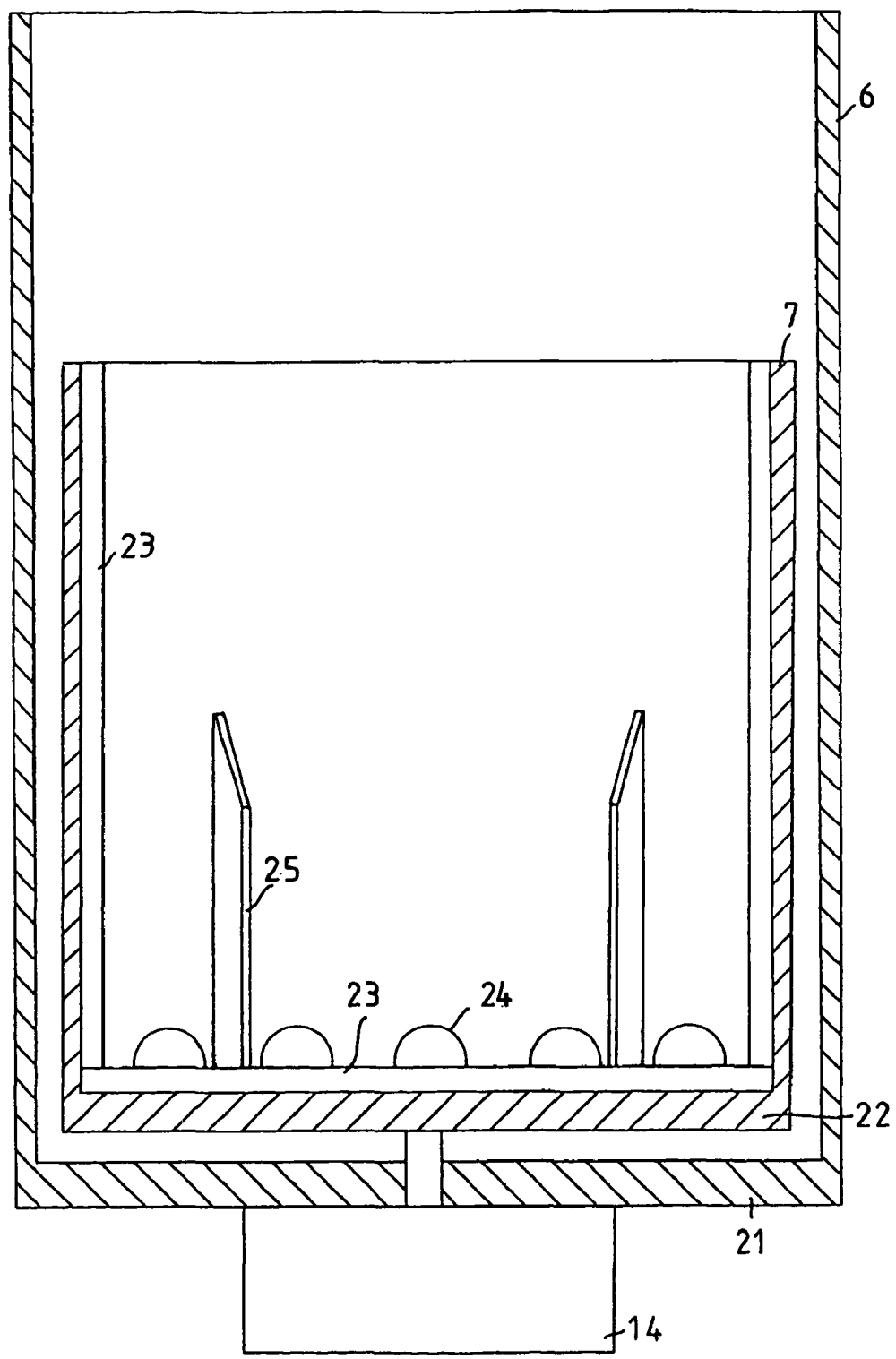
FIG. 5 shows a rotatably disposed drum in schematic cross-section.

FIG. 5 shows a schematic cross-section of a rotatably disposed drum 7 arranged in shell 6. Shell 6 is closed on the rear side by a cover 21 on which the reduction gear box 14 is mounted. Drum 7 is closed on the rear side by a cover 22 to which the output shaft of reduction gear box 14 is fixed. Shell 6, drum 7 and associated covers 21,22 are preferably manufactured from a plastic or stainless steel. Attached to the inside of drum 7 is a layer 23 of rubber or a soft plastic which prevents wear of the dental trays and limits the noise generated by the device. Drum 7 and layer 23 are provided with mutually corresponding holes 24, the diameter of which is chosen such that passing material cannot block pipe 11. In order to prevent the dental trays remaining at the bottom of drum 7 during rotation of the drum, a number of displacing members 25 are preferably placed in drum 7 in the form of strips running in longitudinal direction on the inside.

The invention claimed is:

1. A method for cleaning dental trays at least partly filled with a moulding material, comprising the steps of:
   placing the dental trays in a generally cylindrical container,
   rotating the container about a longitudinal axis, wherein the longitudinal axis encloses an angle of 30° and 60° with a horizontal plane, and
   spraying the dental trays with a cleaning liquid under high pressure, wherein the cleaning liquid is sprayed using a rotating nozzle.

* * * * *